US009789190B2

(12) United States Patent
Garamszegi et al.

(10) Patent No.: US 9,789,190 B2
(45) Date of Patent: Oct. 17, 2017

(54) EMD FORMULATION COMPRISING PGA

(75) Inventors: Laszlo Garamszegi, Basel (CH); Andri Vital, Basel (CH)

(73) Assignee: STRAUMANN HOLDING AG, Basel (CH)

(*) Notice: Subject to any disclaimer, the term of this patent is extended or adjusted under 35 U.S.C. 154(b) by 316 days.

(21) Appl. No.: 13/643,658

(22) PCT Filed: Oct. 17, 2011

(86) PCT No.: PCT/EP2011/068092
§ 371 (c)(1),
(2), (4) Date: Nov. 20, 2012

(87) PCT Pub. No.: WO2012/049324
PCT Pub. Date: Apr. 19, 2012

(65) Prior Publication Data
US 2013/0210735 A1    Aug. 15, 2013

(30) Foreign Application Priority Data
Oct. 15, 2010  (SE) ...................... 1051082

(51) Int. Cl.
| A61Q 11/00 | (2006.01) |
| A61K 38/39 | (2006.01) |
| A61K 47/36 | (2006.01) |
| A61K 8/64  | (2006.01) |
| A61K 6/00  | (2006.01) |
| A61K 9/08  | (2006.01) |
| A61K 8/49  | (2006.01) |

(52) U.S. Cl.
CPC ............ *A61K 47/36* (2013.01); *A61K 6/0038* (2013.01); *A61K 8/498* (2013.01); *A61K 8/64* (2013.01); *A61K 9/08* (2013.01); *A61K 38/39* (2013.01); *A61Q 11/00* (2013.01)

(58) Field of Classification Search
USPC ........................................................ 424/49
See application file for complete search history.

(56) References Cited

U.S. PATENT DOCUMENTS

| 467,032     | A   |   | 1/1892  | Joyce |  |
| 5,098,891   | A   |   | 3/1992  | Hammarstrom et al. | |
| 2002/0169105| A1  | * | 11/2002 | Gestrelius ................ | A61K 8/19 424/549 |
| 2006/0147395| A1  |   | 7/2006  | Lyngstadaas et al. | |
| 2010/0080836| A1  | * | 4/2010  | Busch ..................... | A61L 27/20 424/422 |
| 2010/0104648| A1  | * | 4/2010  | Bjursten ................. | A61L 27/06 424/489 |

FOREIGN PATENT DOCUMENTS

| EP | 0263086 B1     | 12/1991 |
| EP | 0337967 B1     | 5/1993  |
| EP | 1120428 A2     | 8/2001  |
| EP | 1059934 B1     | 7/2002  |
| EP | 1153610 B1     | 8/2003  |
| EP | 1862170 B1     | 3/2012  |
| JP | 06-090703      | 4/1994  |
| JP | 2008523047 A   | 7/2008  |
| JP | 2009029813 A   | 2/2009  |
| WO | WO0053196 A1   | 9/2000  |
| WO | WO0053197 A1   | 9/2000  |
| WO | WO0178688 A1   | 10/2001 |
| WO | WO0197834 A1   | 12/2001 |
| WO | WO02080994 A1  | 10/2002 |
| WO | WO03024479 A1  | 3/2003  |
| WO | WO2006064381 A2| 6/2006  |

OTHER PUBLICATIONS

Maycock et al. Connect Tissue Res, Characterization of a porcine amelogenin preparation, EMDOGAIN, a biological treatment for periodontal disease, 43(2-3) pp. 472-476, 2002.*
Basly, J. P., et al., "Radiosterilization dosimetry by electron-spin resonance spectroscopy: Cefotetan", Analytica Chimica Acta 359 (1998) 107-113.
Hammarstrom, L., et al., "Periodontal regeneration in a buccal dehiscence model in monkeys after application of enamel matrix proteins", J Clin Periodontal 1997, 24, 569-677.
Gestrelius, S. et al., "Emdogain—periodontal regeneration based on biomimicry", Clin. Oral Invest (2000) 4:120-125.
Hammarstrom, L. et al., "Periodontal regeneration in a buccal dehiscence model in monkeys after application of enamel matrix proteins", J. Clin. Periodontal 1997, 24:669-677.
Lyngstadaas, S. et al., "Autocrine growth factors in human periodontal ligament cells cultured on enamel matrix derivative", J. Clin. Periondontal 2001, 28:181-188.
Svensson J. et al., "Histidine tag fusion increases expression levels of active recombinant amelogenin in *Escherichia coli*", Protein expression & Purification 48 (2006) 134-141.
Gray, C. J. et al., "Studies on Chemical Stability of Propylene Glycol Alginate Esters", Carbohydrate Polymers 12 (1990) 419-430.
Nguyen T. Q. et al., "Protective Effect of the Phenyl Group in Irradiated Compatible Blends of Poly(methyl Methacryalte) and Poly(styrene-Co-Acrylonitrile)", Journal of Appl. Pol. Sci., vol. 29, 455-464 (1984).

(Continued)

*Primary Examiner* — Lezah Roberts
(74) *Attorney, Agent, or Firm* — Cermak Nakajima & McGowan LLP; Malcolm K. McGowan

(57) ABSTRACT

Enamel Matrix Derivative (EMD) proteins and enamel matrix proteins are widely used in clinical dentistry because of their ability to promote regeneration of soft and hard tissues and to reduce inflammation and infections. The present invention relates to the surprising finding that a pharmaceutical, dental and/or cosmetic formulation, which comprises purified Enamel Matrix Derivative (EMD) proteins and/or enamel matrix proteins and sterilized Propylene Glycol Alginate (PGA), wherein the sterilized PGA is obtained from non-sterilized PGA having a weight average molecular weight ($M_{wo}$) of between 250-500 kDa, is more stable over time, especially, the pH is more stable over time.

23 Claims, 11 Drawing Sheets

(56) References Cited

OTHER PUBLICATIONS

Figure 1:
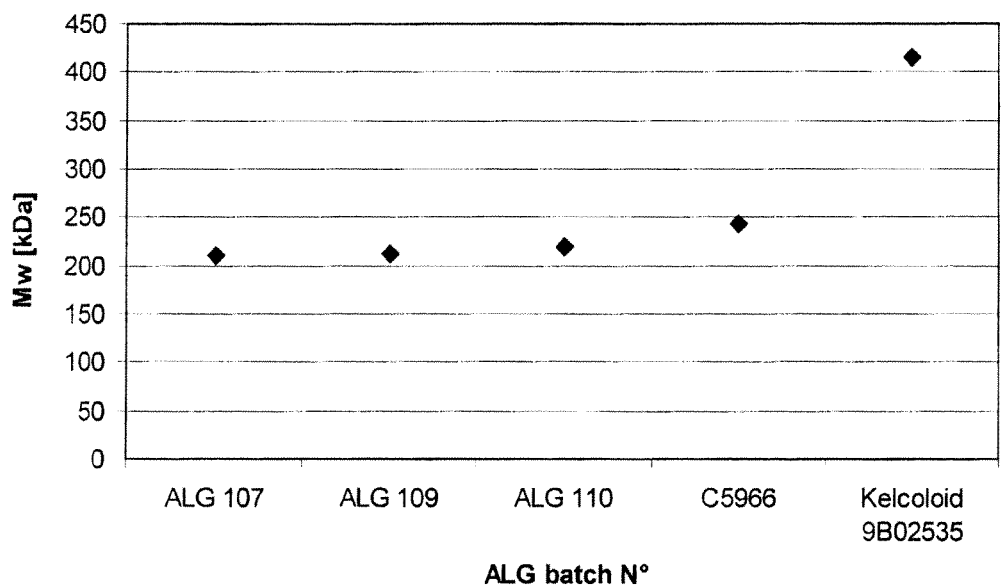

Lyngstadaas S. P. et al., "Enamel matrix proteins; old molecules for new", Orthod Craniofac Res Aug. 2009 12(3):243-253.
Gestrelius S. et al., "Formulation of enamel matrix derivative for surface coating", J. Clin. Periodontal 1997 (24) 678-684.
Heiji L. et al., "Periodontal regeneration with enamel matrix derivative in one human experimental defect", J. Clin Periodontal 1997 )24) 693-696.
Kenny D. J. et al., "Clinical Management of Avulsed Permanent Incisors Using Emdogain: Initial Report of an Investigation", Journal de l'Assoc denttarie canadienne, vol. 26, No. 1, Jan. 2000.
Bratthall G. et al., "Comparison of ready-to-use EMDOGAIN-gel and EMDOGAIN in patients with chronic adult periodontitis", J. Clin Periodontal 2001: 28:923-929.

\* cited by examiner

EMD FORMULATION COMPRISING PGA

TECHNICAL FIELD OF THE INVENTION

The present invention relates to a pharmaceutical, dental and/or cosmetic formulation comprising purified enamel matrix proteins and/or enamel matrix derivative (EMD) proteins. In particular, the present invention is related to stable formulations comprising enamel matrix proteins and/or enamel matrix derivative (EMD) proteins and sterilized propylene glycol alginate (PGA) having a weight average molecular weight of at least 130 kDa.

BACKGROUND ART

Enamel matrix proteins, present in the enamel matrix, are most well-known as precursors to enamel. Prior to cementum formation, enamel matrix proteins are deposited on the root surface at the apical end of the developing tooth-root. There is evidence that the deposited enamel matrix is the initiating factor for the formation of cementum. Again, the formation of cementum in itself is associated with the development of the periodontal ligament and the alveolar bone. Enamel matrix proteins can therefore promote periodontal regeneration through mimicking the natural attachment development in the tooth (Gestrelius S, Lyngstadaas S P, Hammarström L. Emdogain—periodontal regeneration based on biomimicry. Clin Oral Invest 4:120-125 (2000)).

Isolated enamel matrix proteins are able to induce not only one, but an orchestrated cascade of factors, naturally found in tissues developing adjacent to the enamel matrix. They mimic the natural environment of a developing tissue and thus mimic a natural stimulation for tissue regeneration, cell differentiation and/or maturation.

Enamel matrix derivative (EMD), in the form of a purified acid extract of proteins from pig enamel matrix, has previously been successfully employed to restore functional periodontal ligament, cementum and alveolar bone in patients with severe tooth attachment loss (Hammarström et al., 1997, Journal of Clinical Periodontology 24, 658-668).

Enamel matrix derivative (EMD) formulations have also been shown to promote periodontal regeneration (Hammarström et al., 1997, Journal of Clinical Periodontology 24, 669-677). In this study different formulations were used in order to find out if the result would differ depending on which formulation was used. The study showed that the most satisfactory result was given when EMD was dissolved in PGA.

For example, U.S. Pat. No. 5,098,891 describes for the first time a composition for use in inducing binding between parts of mineralized tissue by regeneration of mineralized tissue on at least one of the parts, containing as an active constituent a protein fraction originating from a precursor to dental enamel, so called enamel matrix.

Furthermore, in studies on cultured periodontal ligament cells (PDL), it was shown that the attachment rate, growth and metabolism of these cells were significantly increased when EMD was present in the cultures. Also, cells exposed to EMD showed increased intracellular cAMP signaling and autocrine production of growth factors when compared to controls. Epithelial cells, on the other hand, although increasing cAMP signaling and growth factor secretion when EMD was present, were inhibited in both proliferation and growth (Lyngstadaas et al., 2001, Journal of Clinical Periodontology 28, 181-188).

Enamel matrix proteins and enamel matrix derivatives (EMD) proteins have previously been described in the patent literature to be able to induce hard tissue formation (i.e. enamel formation, U.S. Pat. No. 4,672,032 (Slavkin)), endorse binding between hard tissues (EP-B-0 337 967 and EP-B-0 263 086), promote open wound healing, such as of skin and mucosa, have a beneficial effect on treatment of infections and inflammatory diseases (EP-B-1059934 and EP-B-1153610), induce regeneration of dentin (WO 01/97834), promote the take of a graft (WO 00/53197), induce apoptosis in the treatment of neoplasms (WO 00/53196), regulate imbalance in an immune response to a systemic infection or inflammation (WO 03/024479), and to facilitate filling a wound cavity and/or tissue defect following from a procedure and/or trauma, such as a cytoreductive surgery (WO 02/080994).

EMD is composed of a number of proteins, such as amelogenins, enamelin, tuft protein, proteases, and albumin. Amelogenins, a major constituent of EMD, at least up to 60%-90%, such as 70-90%, are a family of hydrophobic proteins derivable from a single gene by alternative splicing and controlled post secretory processing. They are highly conserved throughout vertebrate evolution and demonstrate a high overall level of sequence homology among all higher vertebrates examined (80%). In fact, the sequences of porcine and human amelogenin gene transcript differ only in 4% of the bases. Thus, enamel matrix proteins and/or EMD proteins, although of porcine origin, are considered "self" when encountered in the human body and can promote dental regeneration in humans without triggering allergic responses or other undesirable reactions. Enamel Matrix Derivative Protein (EMD) is the most known precursor to enamel. Its aqueous solution thickened with PGA is commercialized under the trade-name Straumann® Emdogain. Enamel Matrix Derivative Protein (EMD) aqueous solution thickened with PGA can also be found in Straumann® Emdogain Plus.

In order to keep the EMD in aqueous solution, the solution should have a pH well-below the protein isoelectric point (IEP), for EMD the IEP is pH 6.5, hence, more preferred is that the pH of the solution is <5.0. For easy application, the solution is thickened by PGA. Chemically, the PGA is an ester of alginic acid, which is derived from kelp (seaweed). Some of the carboxyl groups are esterified with propylene glycol, some are neutralized with an appropriate alkali, and some remain free. The PGA itself is acidic and the pH decreases after the PGA is dissolved in the EMD solution. Under acidic conditions, the pH keeps decreasing due to the degradation of PGA. The durability of the mixture is determined by the pH value at which the EMD is capable to precipitate onto the tooth surface. It is considered that the precipitation occurs in physiological conditions, i.e. pH near IEP. The pH and buffering capacity of both the tooth root environment and the EMD-PGA mixture influences the precipitation behavior of the EMD proteins, a pH near IEP and a lower buffering capacity of the EMD solution formulated with PGA favors the precipitation.

D. J. McHugh describes in HYPERLINK http://www.fao.org/docrep/x5822e/x5822e04.htm, that the degree of polymerization (DP) of an alginate is a measure of the average molecular weight of the molecules and is the number of uronic acid units per average chain. DP and molecular weight relate directly to the viscosity of alginate solutions; loss of viscosity on storage is a measure of the extent of de-polymerization of the alginate.

PGA is produced in various grades, which are usually described as low, medium and high viscosity alginates (referring to the viscosity in 2% aqueous solution). The higher the molecular weight of a PGA alginate, the greater the viscosity of its solution. Manufacturers can control the molecular weight (degree of polymerization, DP) by varying the severity of the extraction conditions and they offer products ranging from 10-1000 mPa·s (1% solution) with a DP range of 100-1 000 units. PGA of viscosity 200-400 mPa·s, "medium viscosity", probably finds the widest applications. PGAs with a high DP are known to be less stable than those with a low DP. Low viscosity PGA (up to about 50 mPa·s) has been stored at 10-20° C. with no observable change in 3 years. Medium viscosity sodium alginates (up to about 400 mPa·s) show a 10% loss at 25° C. and 45% loss at 33° C. after one year, and higher viscosity alginates are even less stable.

Propylene glycol alginates showed about 40% loss in viscosity after a year at 25° C. and also became less soluble. Ammonium alginate is generally less stable than any of the above. Alginic acid is the least stable of the products and any long chain material degrades to shorter chains within a few months at ambient temperatures. However, alginates comprising short chain material are stable and alginic acid with a DP of about 40 units of uronic acid per chain will show very little change over a year at a temperature of 20° C. However, the main use of alginic acid, as a disintegrant in pharmaceutical tablets, depends on its ability to swell when wetted and this is not affected by changes in DP. The commercial alginates should be stored in a cool place, i.e. at temperatures of 25° C. or lower as elevated temperatures can cause significant depolymerization, affecting the commercially useful properties, such as viscosity and gel strength. Said alginates usually contain 10-13% moisture and the rate of depolymerization increases as the proportion of moisture is increased, thus the storage area should be dry.

As mentioned above, EMD proteins have prior been formulated in an aqueous solution with PGA, wherein the degradation of PGA provides acidic products, which in turn decreases the pH over time. At elevated temperatures, the degradation accelerates. In order to avoid the accelerated acidification of the product, and thus to limit this effect, the products have to be transported and stored at low temperatures, i.e. at a temperature range of 2 to 8° C. Nonetheless, the stability of EMD in the commercially available Straumann® Emdogain formulation with PGA has been known to decrease rapidly over time.

SUMMARY OF INVENTION

Enamel Matrix Derivative (EMD) proteins and enamel matrix proteins are widely used in clinical dentistry because of their ability to promote regeneration of soft and hard tissues and to reduce inflammation and infections.

Straumann® Emdogain is a commercially available product composed of an alginate carrier, Propylene Glycol Alginate (PGA), and porcine Enamel Matrix Derivative (EMD) proteins and is used in the treatment of periodontal diseases and has repeatedly been shown to promote hard and soft tissue regeneration and decrease inflammation following periodontal surgery. The PGA employed in the manufacture of Straumann® Emdogain has a viscosity 50-175 mPa·s (in 2% aqueous solution 22° C. Brookfield viscosity), i.e. of "lower viscosity". The formulation suffers from a lack of stability due to the rapid decrease of pH over time.

Thus, the formulation has to be stored and transported at low temperatures, i.e. temperatures in the range of 2 to 8° C., in order to avoid the accelerated acidification of the formulation.

The present invention relates to the surprising finding that a pharmaceutical, dental and/or cosmetic formulation, which comprises purified Enamel Matrix Derivative (EMD) proteins and/or enamel matrix proteins and sterilized Propylene Glycol Alginate (PGA), wherein the sterilized PGA is obtainable from e-beam sterilization of non-sterilized PGA having a weight average molecular weight ($M_{W0}$) of between 250-500 kDa, is more stable over time, especially the pH of the formulation is more stable over time.

FIGURES

FIG. 1 Weight average molecular weight ($M_W$) of raw PGA since 2002 to 2009 and Kelcoloid® O (PGA)

Figure 2:
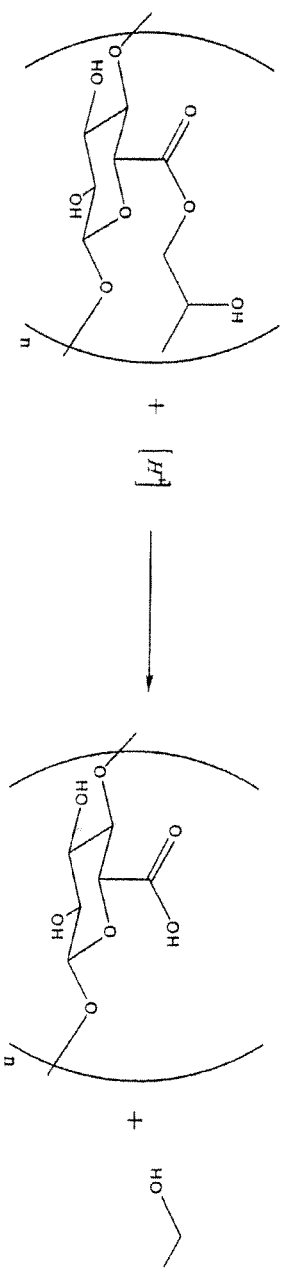

FIG. 2 Reaction scheme of acid catalyzed hydrolyses of PGA

Figure 3:
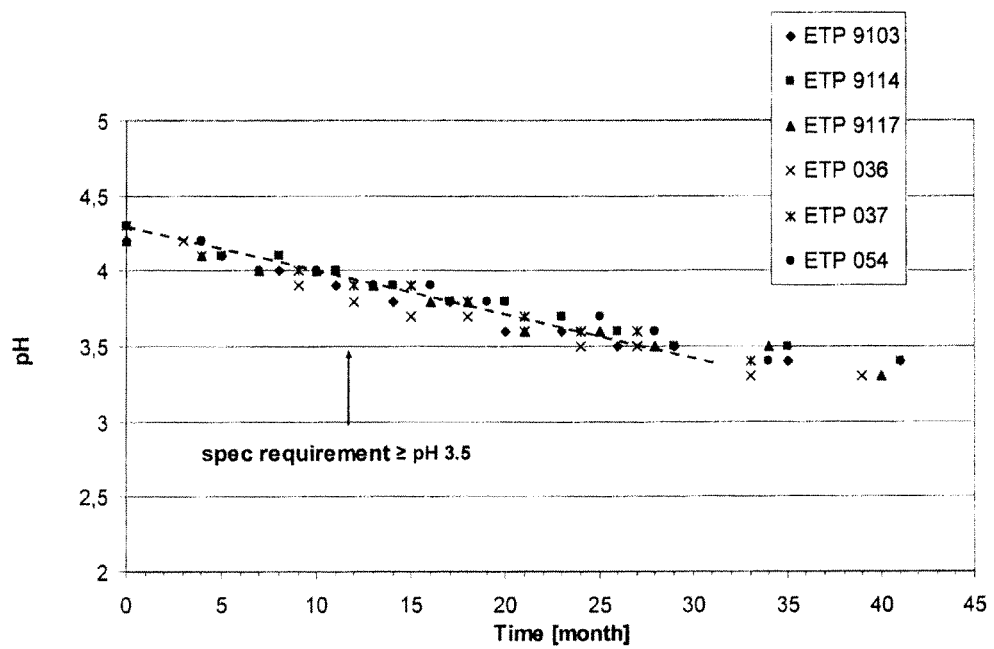

FIG. 3 pH of Straumann® Emdogain vs. storage time at 2-8° C.

Figure 4:
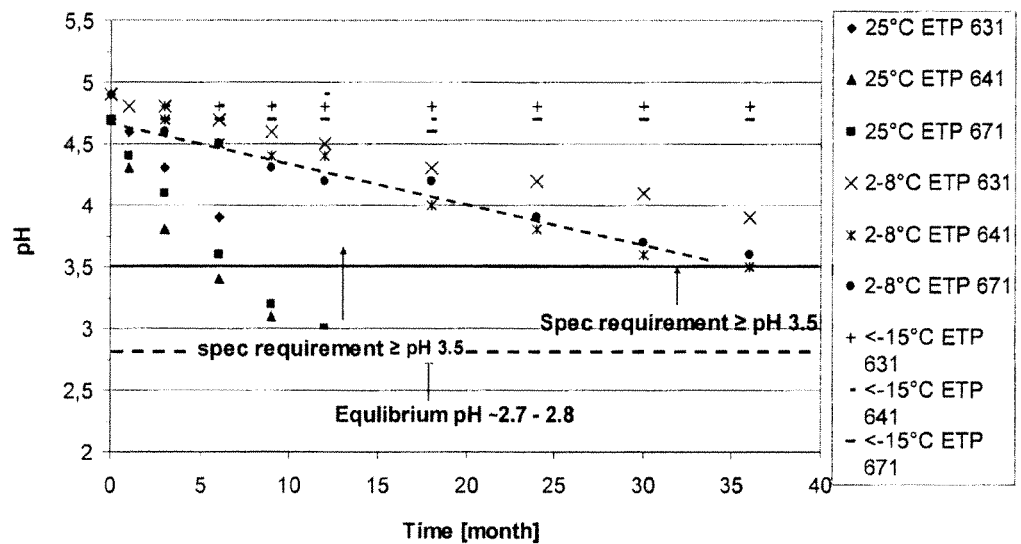

FIG. 4 pH of Straumann® Emdogain vs. storage time at different temperatures

Figure 5:
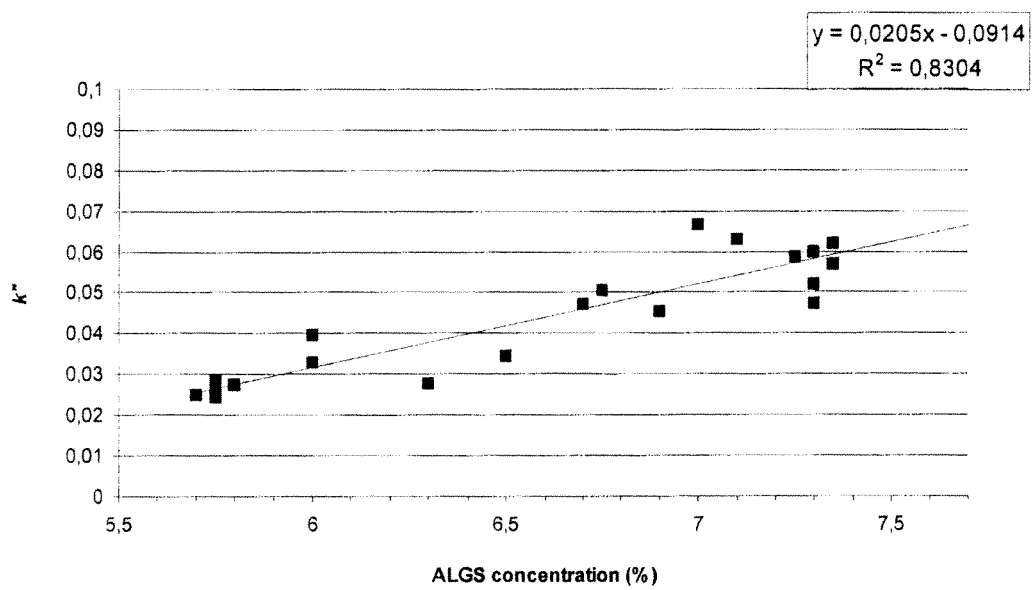
Figure 6A:
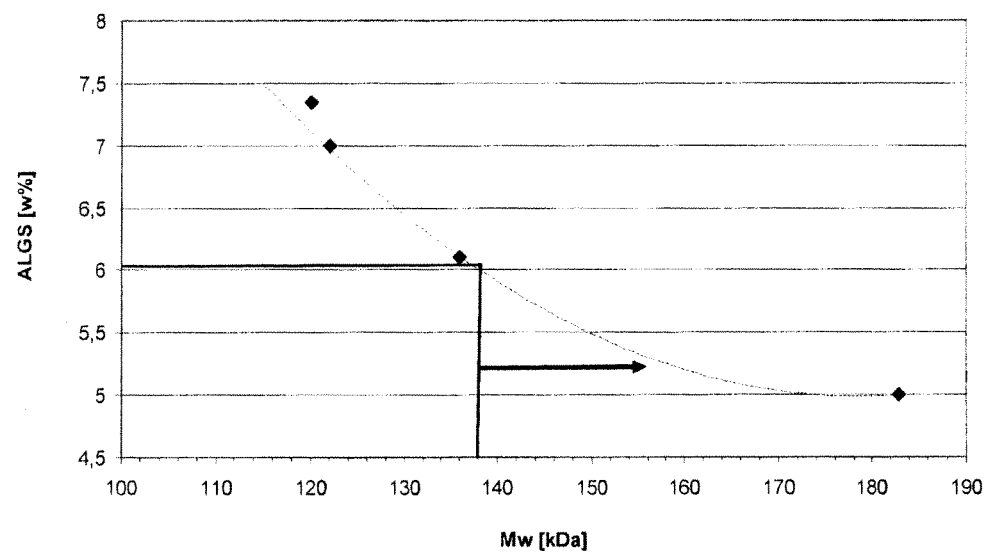
Figure 6B:
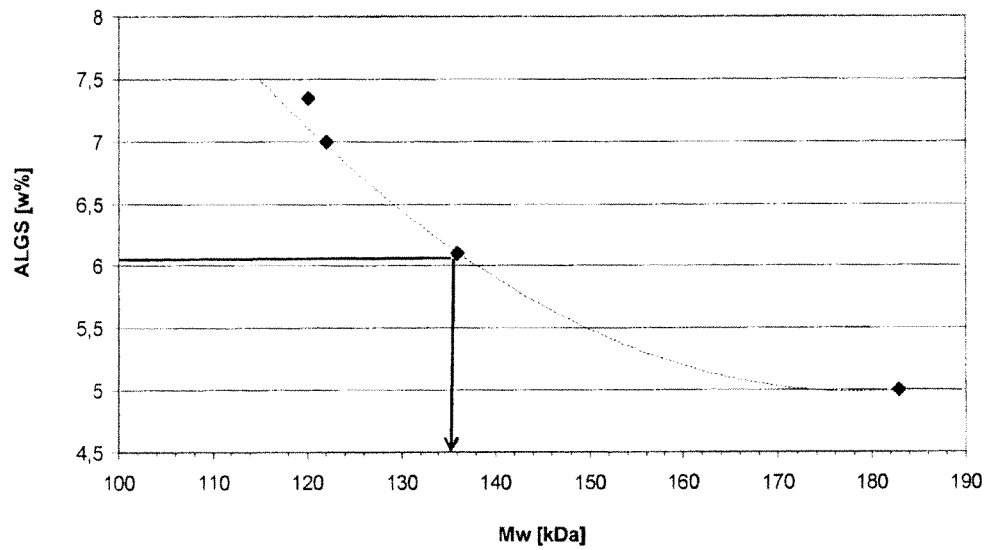

FIG. 5 Pseudo first order reaction rate constant dependence from PGA concentration 2-5° C. range FIG. 6 The threshold of the weight average molecular weight of PGA can be above 135 kDa (FIG. 6A) and above 140 kDa (FIG. 6B) measured by GPC to Pollulan calibration standard.

Figure 7:
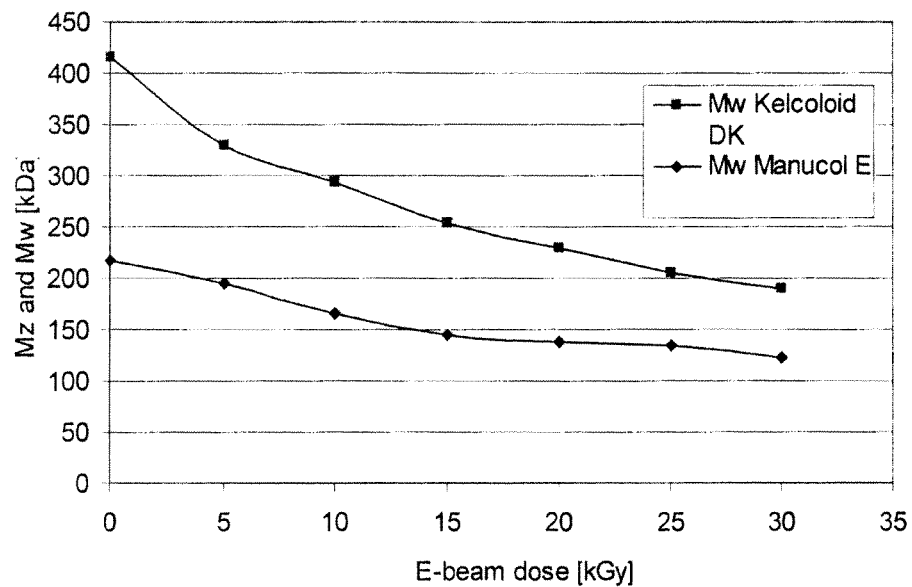

FIG. 7 Comparative Manucol® ester B-Kelcoloid® O. molar mass ($M_W$) as a function of sterilization e-beam dose.

Figure 8:
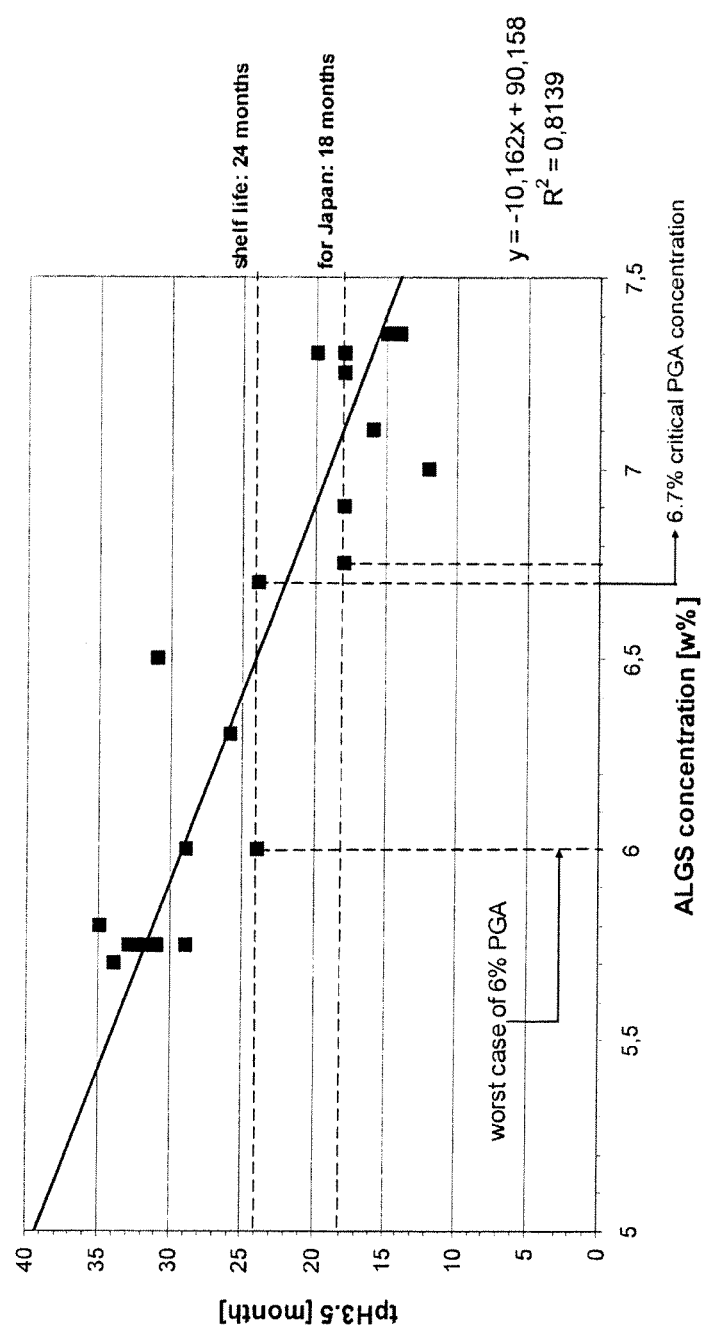

FIG. 8 The figure shows the relationship between the PGA concentration and the durability of Straumann® Emdogain-pH spec (3.5) determined shelf life of Emdogain vs. sterilized PGA (i.e. e-beam sterilized PGA) concentration.

Figure 9:
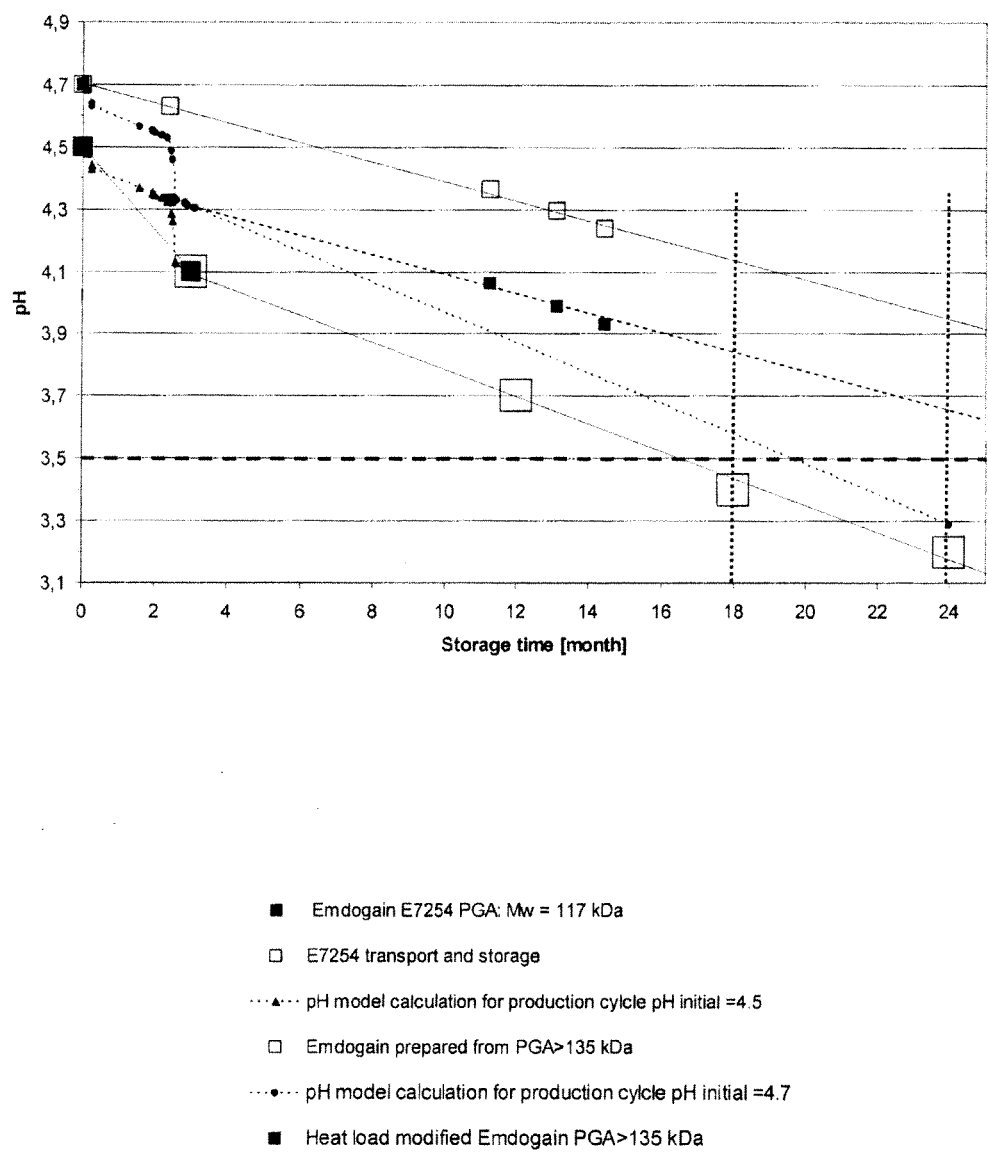

FIG. 9 The figure shows the relationship between the molecular weight ($M_W$) of sterilized PGA and the storage stability of Emdogain when the $M_W$ of the sterilized PGA is above 135 kDa, such as 185 kDa. As a reference a sterilized PGA with a $M_W$ of 117 kDa is used.

Figure 10:
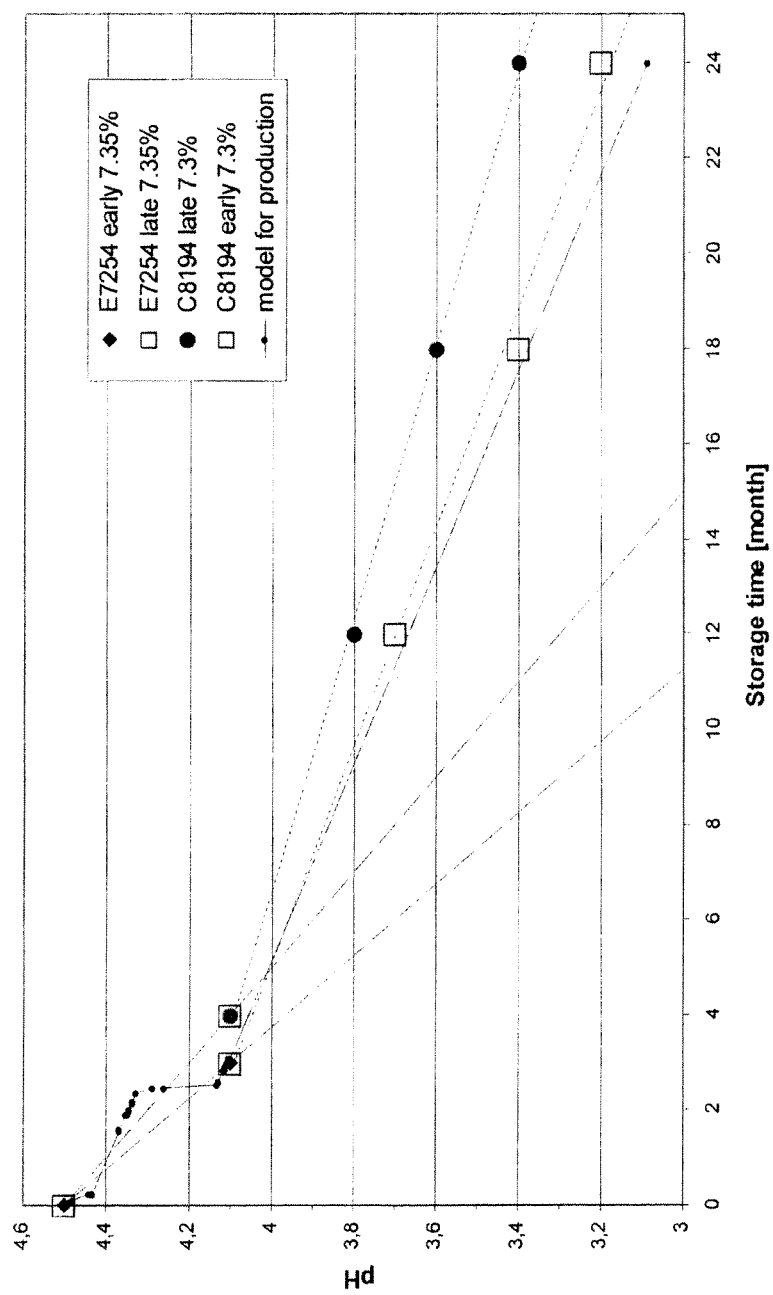

FIG. 10 The figure shows the relationship between the molecular weight ($M_W$) of sterilized PGA and the storage stability of Emdogain when the $M_W$ of the sterilized PGA is 135 kDa.

DEFINITIONS

ALG is the abbreviation used herein for non-sterilized PGA.

ALGS is the abbreviation used herein for sterilized PGA, which has been sterilized by using e-beam.

In the present context "subject" relate to any vertebrate animal, such as bird, reptiles, mammals, primates and humans.

PGA has several different names: Propylene glycol alginate, Hydroxypropyl alginate, Propane 1,2-diol alginate or E405.

In the present context "formulation" can be replaced by "composition".

In the present context "e-beam" means electron beam, also called cathode rays, which are streams of electrons. E-beam sterilization is used as a disinfestation method.

The term non-sterilized propylene glycol alginate (PGA) is in the present context intended to include food grade PGA, raw PGA, medical grade PGA and technical grade PGA.

The sterilized propylene glycol alginate (PGA) is herein preferably obtained from e-beam sterilization of non-sterilized PGA having a weight average molecular weight ($M_{W0}$) of at least 250 kDa, such as of between 250-500 kDa. Alternatively, and interchangeably, the sterilized PGA is obtainable from e-beam sterilization of non-sterilized PGA with an initial weight average molecular weight ($M_{W0}$) of at least 250 kDa. The weight average molecular weight ($M_w$) of the sterilized PGA is more than 130 kDa, such as between 130-500 kDa.

Sterilization in the present context can be achieved by the non-sterilized PGA being prepared and sterilized by using a dose in the range of about 25 to 30 kGy, said dose should at least be 25 kGy. The sterilisation method comprises the following steps: 1) the sterility assurance level (SAL) is selected ($10^{-6}$), 2) the total bioburden for the sample to be sterilized is calculated, 3) the sample is sterilized using an e-beam. The selection of the e-beam dose is based on the calculation of step 2). The method follows the recommendations of ISO 11137-2 (2006). The term "sterility assurance level" is the probability of a single viable microorganism occurring on an item after sterilization and the term "bioburden" is the population of viable microorganism on or in a product. Said PGA is sterilized as a powder and the obtained product is mixed with excipient under aseptic environment. Alternatively, a powder of non-sterilized PGA is mixed with excipients under aseptic environment and then sterilized. However, other commonly known sterilization methods can be used for sterilizing a non-sterilized PGA or a mixture comprising a non-sterilized PGA as a person skilled in the art is aware of.

It is to be understood throughout the present context that even though exact values are given, these values also include derivations from these values.

The weight average molecular weight of the PGA (both the sterilized and the non-sterilized) is in the present invention determined by size exclusion chromatography using Pollulan molar mass standards, however, when other methods, such as universal calibration, determination of intrinsic viscosity etc., are used for determination, the weight average molecular weight may be specified in other terms and have other values as a person skilled in the art is aware of.

DETAILED DESCRIPTION OF INVENTION

The present invention relates to the surprising finding that a pharmaceutical, dental and/or cosmetic formulation, which comprises purified Enamel Matrix Derivative (EMD) proteins and/or enamel matrix proteins and sterilized Propylene Glycol Alginate (PGA), wherein the sterilized PGA is obtained from non-sterilized PGA having an initial weight average molecular weight ($M_{w0}$) of between 250-500 kDa, is more stable over time, especially the pH is more stable over time. The weight average molecular weight of the sterilized PGA is more than 130 kDa, such as between 130-500 kDa. The sterilized PGA may be obtained from e-beam sterilization.

The PGA employed in the manufacture of prior known formulations comprising purified Enamel Matrix Derivative (EMD) proteins and/or enamel matrix proteins and sterilized Propylene Glycol Alginate (PGA) has a viscosity 50-175 mPa·s (2% aqueous solution 22° C. Brookfield viscosity), i.e. it is of "lower viscosity". These formulations suffer from a lack of stability due to the rapid decrease of pH over time even at low temperatures. Thus, the product has to be stored and transported at low temperatures, i.e. temperatures in the range of 2 to 8° C., in order to avoid the accelerated acidification of the product. Furthermore, said PGAs had an initial weight average molecular weight that was between 210 to 245 kDa, meaning about 230 kDa, or no more than 245 kDa (see Table 1).

It has now surprisingly been found that formulations comprising sterilized propylene glycol alginate molecules (PGA) having a high weight average molecular weight are more stable and have a less temperature sensitive pH. This leads to more storage stable formulations over time. Examples of propylene glycol alginate having a high weight average molecular weight are those sold under the trade names Kelcoloid® O, Kelcoloid® NF and Manucol® Ester M. Kelcoloid® O batch No 9B02535 is an additional example of a propylene glycol alginate molecules having a high weight average molecular weight.

In addition to Kelcoloid® O, there are different grades of Kelcoloid®: s available, such as Kelcoloid® with the product names: Kelcoloid® HVF, Kelcoloid® LVF and Kelcoloid® S. The grades, according to their product sheet, differentiate mainly from each other in viscosity, esterification degree and pH in aqueous solution. The esterification degree of said PGA:s is high, such as above 70, such as above 80.

The present invention is based on the surprising finding that different PGA:s, which fulfill all pharmacopoeial requirement and have the same viscosity, the same initial pH and about the same degree of esterified carboxyl groups, which are used and are to be used in the Straumann® Emdogain formulations and Straumann® Emdogain Plus formulations may result in different storage stability over time. This surprising finding owns to that the pH stability of the end products depends on the quality of the used PGA related to the weight average molecular weight of PGA. Hence, a relationship between the acid catalysed hydrolyses rate of PGA and the weight average molar weight of the carrier PGA has surprisingly been found.

The present invention is thus based on the surprising finding that more stable and longer shelf life formulations can be obtained by carefully selecting the degree of PGA used in said formulations. Also, the present invention is based on the finding that a formulation comprising purified Enamel Matrix Derivative (EMD) proteins and/or enamel matrix proteins and a PGA having a higher initial weight average molecular weight than those previously used, will be more stable and have a longer durability.

Thus, one problem that can be avoided by the formulations of the present invention and the use of a specific quality of PGA is that the storage period and durability for said formulations can be guaranteed. From an economical point of view it is advantageous to specify and measure the molecular weight of the PGA used in the formulation, thereby keeping a long expire date of the formulation package.

It has now been found that a quality of PGA with a higher weight average molecular weight ($M_w$), i.e. a weight average molecular weight when sterilized is above 130 kDa, such as a weight average molecular weight in the range of 130 to 500 kDa, 130 to 450 kDa, 130 to 420 kDa, 200 to 450 kDa, or 130 to 250 kDa, is desirable in formulations comprising EMD proteins and/or enamel matrix proteins. Said weight average molecular weight can also be in the range of 130 to 550 kDa. The weight average molecular weight can also be above 130 kDa, such as above or equal 135, 140, 150, 180 or 185 kDa.

The pH stability is the most important parameter of formulations comprising EMD proteins and/or enamel matrix proteins and PGA and influences the durability of the product and also has a significant impact on the transport, i.e. how the formulations are transported in regard of temperature and time. The pH decreases over time and how speed of the decrease will influence the durability of the formulations, the faster the pH is decreased, the faster the formulations reduce their stability.

Furthermore, it has also surprisingly been found that using a PGA having a higher weight average molecular weight, in formulations comprising EMD proteins and/or enamel matrix proteins, will provide said formulations with better thickening (gelforming) behavior. Also, using a PGA having a higher weight average molecular weight will provide said formulations with better pH stability as less concentration of PGA is needed. According to the present invention, the concentration of sterilized PGA in the claimed formulations are no more than 6 weight/volume % (w/v %). Furthermore, the concentration of sterilized PGA is in the range of 3 to 6 w/v %, such as 3 to 5 w/v %, such as 3 to 4 w/v %. Furthermore, the concentration of sterilized PGA is such as 3, 3.5, 4, 4.5, 5, 5.5 or 6 w/v %.

The present invention therefore relates to a stable, such as a storage stable pharmaceutical, dental and/or cosmetic formulation comprising enamel matrix proteins and/or enamel matrix derivative (EMD) proteins, wherein said formulation comprises no more than 6 weight/volume % (w/v %), such as in the range of 3 w/v % to 6 w/v %, sterilized propylene glycol alginate (PGA) and wherein said sterilized PGA has a weight average molecular weight ($M_W$) above 130 kDa, such as above or equal 135, 140, 150, 180 or 185 kDa, such as in the range of between 130-250 kDa.

In particular, said pharmaceutical, dental and/or cosmetic formulation is a formulation, wherein the enamel matrix proteins and/or enamel matrix derivative proteins comprise at least 60 to 90% amelogenin, such as at least 60, 61, 62, 63, 64, 65, 66, 67, 68, 69, 70, 80 or 90%, having an average molecular weight selected from the group consisting of between 18 and 25 kDa, between 20 and 24 kDa, between 20 and 22 kDa, and 20 kDa.

The pharmaceutical, dental and/or cosmetic formulation according to the present invention is more stable over time than currently available similar formulations comprising enamel matrix proteins and/or enamel matrix derivative (EMD) proteins, i.e. it has a pH value above pH 3.5 over a period of at least 18 months, such as at least 24 months, such as 18, 19, 20, 21, 22, 23, 24, 25, 26, 27, 28, 29 and 30 months, preferably at a temperature in the range of 2 to 8° C., however higher temperatures can be used as well. According to one embodiment of the invention, a pharmaceutical, dental and/or cosmetic formulation according to the present invention is stable the i.e. it has a pH value above pH 3.5 over a period of at least 34 months, such as at least 36 months.

The pharmaceutical, dental and/or cosmetic formulation according to the present invention is more stable over time than currently available similar formulations comprising enamel matrix proteins and/or enamel matrix derivative (EMD) proteins, i.e. it has a pH value above pH 3.5 over a period of at least 18 months, such as at least 24 months. The formulation of the present invention is preferably kept at a temperature in the range of 2 to 8° C. However, the formulation of the present invention can be kept at higher temperatures as well.

The sterilized PGA is obtained from e-beam sterilization of non-sterilized PGA. Thus, in one embodiment, the present invention, in particular, relates to a pharmaceutical, dental and/or cosmetic formulation comprising enamel matrix proteins and/or enamel matrix derivative (EMD) proteins and sterilized propylene glycol alginate (PGA), wherein the sterilized PGA is obtained from e-beam sterilization of non-sterilized PGA having an initial weight average molecular weight ($M_{W0}$) of at least 250 kDa, such as from e-beam sterilization of non-sterilized PGA with an initial weight average molecular weight ($M_{W0}$) in the range of 250 to 500 kDa. The applied e-beam sterilization dose is in the present context selected from a dose in the range of about 25 to 30 kGy, said dose is at least 25 kGy.

Further, the present invention discloses for the first time and thus relates to a process of producing a pharmaceutical, dental and/or cosmetic formulation, said process is characterized by isolating enamel matrix proteins and/or enamel matrix derivative (EMD) proteins from a developing mammal's teeth, e-beam sterilizing non-sterilized PGA with an initial weight average molecular weight ($M_{W0}$) above 250 kDa, and mixing both components.

Consequently, the present invention also relates to a pharmaceutical, dental and/or cosmetic formulation, comprising enamel matrix proteins and/or enamel matrix derivative (EMD) proteins and sterilized propylene glycol alginate (PGA) with an weight average molecular weight above 130 kDa, such as above or equal 135, 140, 150, 180 or 185 kDa, wherein said formulation is produced by a process comprising isolating enamel matrix proteins and/or enamel matrix derivative (EMD) proteins from a developing mammals teeth, e-beam sterilizing non-sterilized PGA with an initial weight average molecular weight ($M_{W0}$) in the range of 250 to 500 kDa, and mixing both components.

In one embodiment, the present invention relates to the use of an e-beam sterilized non-sterilized PGA with an initial weight average molecular weight ($M_{W0}$) in the range of 250-500 kDa for manufacturing a pharmaceutical, dental and/or cosmetic formulation, comprising enamel matrix proteins and/or enamel matrix derivative (EMD) proteins and sterilized propylene glycol alginate (PGA), wherein the weight average molecular weight ($M_W$) of the sterilized PGA is above 130 kDa, such as above or equal 135 kDa, such as above or equal 185 kDa, and wherein said formulation has a pH value above 3.5 over a period of at least 18 months, such as at least 24 months, such as 19, 20, 21, 22, 23, 24, 25, 26, 27, 28, 29 and 30 months. The formulation is preferably kept at a temperature in the range of 2 to 8° C. However, higher temperatures can be used as well.

The present invention also relates to the use of an e-beam sterilized non-sterilized PGA with an initial weight average molecular weight ($M_{W0}$) in the range of 250-500 kDa for manufacturing a pharmaceutical, dental and/or cosmetic formulation, comprising enamel matrix proteins and/or enamel matrix derivative (EMD) proteins and sterilized propylene glycol alginate (PGA), wherein the weight average molecular weight ($M_W$) of the sterilized PGA is above 130 kDa, such as at least 135 kDa, such as at least 185 kDa, and wherein said formulation has a pH value above 3.5 over a period of at least 18 months, such as at least 24 months. The formulation is preferably kept at a temperature in the range of 2 to 8° C. However, higher temperatures can be used as well.

A pharmaceutical, dental and/or cosmetic formulation according to the present invention, comprises enamel matrix proteins and/or enamel matrix derivative (EMD) proteins in the range of 93% to about 98%, of 94% to about 97%, and of 95% to about 96%, by weight/volume, based on the total combined weight of the matrix proteins and/or enamel matrix derivative (EMD) proteins and the sterilized PGA, not including other excipients.

The invention also relates to a pharmaceutical formulation comprising EMD proteins and/or enamel matrix proteins and PGA, wherein the PGA before sterilization has a weight average molecular weight ($M_{W0}$) in the range of 250-500 kDa or a combination of two or more EMD proteins as defined herein. Such a pharmaceutical formulation optionally also comprises a pharmaceutically acceptable carrier, excipient and/or diluent.

In one embodiment, a pharmaceutical, dental and/or cosmetic formulation according to the present invention further comprises at least two surface stabilizers, which can be selected from the group consisting of anionic surface stabilizer, cationic surface stabilizer, zwitterionic surface stabilizer and ionic surface stabilizer.

The pharmaceutical, dental and/or cosmetic formulation according to the present invention can be used in medicine. For such an intended use, said formulation can be formulated for any administration selected from the group consisting of oral, pulmonary, rectal, opthalmic, colonic, parenteral, intracisternal, intravaginal, intraperitoneal, local, buccal, nasal, and topical administration. According to its intended administration route, the formulation is formulated into a dosage form selected from the group consisting of liquid dispersions, oral suspensions, gels, aerosols, ointments, creams, controlled release formulations, fast melt formulations, lyophilized formulations, tablets, capsules, delayed release formulations, extended release formulations, pulsatile release formulations, and mixed immediate release and controlled release formulations.

Further, a pharmaceutical, dental and/or cosmetic formulation according to the present invention can comprises one or more pharmaceutically acceptable excipient(s), pharmaceutically acceptable carrier(s), or a combination thereof as well as one or more non-enamel matrix proteins and/or enamel matrix derivative (EMD) proteins active agents.

Pharmaceutical formulation in the present context also embraces cosmetic compositions as well as compositions belonging to the so-called grey area between pharmaceuticals and cosmetics, namely cosmeceuticals.

The pharmaceutical formulations may be in form of, e.g., solid, semi-solid or fluid formulations such as, e.g.
  delivery devices, implants;
  powders, granules, granulates, capsules, agarose or chitosan beads, microspheres, nanoparticles;
  sprays, aerosols, inhalation devices;
  gels, hydrogels, pastes, ointments, creams, soaps, tooth paste;
  solutions, dispersions, suspensions, emulsions, mixtures, lotions, mouthwash, shampoos, enemas;
  kits containing e.g. two separate containers, wherein the first one of the containers comprises a formulation of the invention optionally admixed with other active drug substance(s) and/or pharmaceutically acceptable excipients, carriers and/or diluents and the second container comprises a suitable medium intended to be added to the first container before use in order to obtain a ready-to-use formulation.

A formulation of the invention may be suitable for use during surgery, e.g. for local application (e.g. in the oral cavity) in the form of a gel, film or dry pellet, or as a rinsing solution or treatment with a paste or cream.

The formulations may be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988.

The formulations of the invention may e.g. be applied on dentures, prostheses, implants, and to body cavities such as the oral, nasal and vaginal cavity, especially, application within the dental/odontologic area is envisioned.

A pharmaceutically or cosmetically acceptable excipient, carrier and/or diluent is a substance which is substantially harmless to the individual to which the formulation is to be administered. Such an excipient, carrier and/or diluent normally fulfill the requirements given by the national health authorities. Official pharmacopoeias such as e.g. the British Pharmacopoeia, the United States of America Pharmacopoeia and The European Pharmacopoeia set standards for pharmaceutically acceptable excipients.

Whether a pharmaceutically acceptable excipient is suitable for use in a pharmaceutical formulation is generally dependent on which kind of dosage form is chosen. In the following are given examples of suitable pharmaceutically acceptable excipients for use in different kinds of formulation s for use according to the invention.

The choice of pharmaceutically acceptable excipient(s) in a composition for use according to the invention and the optimum concentration thereof cannot generally be predicted and must be determined on the basis of an experimental evaluation of the final composition. However, a person skilled in the art of pharmaceutical formulation can find guidance in e.g., "Remington's Pharmaceutical Sciences", 18th Edition, Mack Publishing Company, Easton, 1990.

The pharmaceutically acceptable excipients may include solvents, buffering agents, preservatives, humectants, chelating agents, antioxidants, stabilizers, emulsifying agents, suspending agents, gel-forming agents, ointment bases, penetration enhancers, perfumes, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, and tea seed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethylamine etc.

Suitable examples of preservatives for use in formulation s according to the invention are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalkonium chloride, and benzylalcohol, or mixtures of preservatives.

Examples of humectants are glycerin, propylene glycol, sorbitol, lactic acid, urea, and mixtures thereof.

Examples of chelating agents are sodium EDTA and citric acid.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin; sorbitan monooleate derivatives; wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., sodium carboxymethyl cellulose, hydroxyethylcellulose, hydroxypropylcellulose, hydroxypropylmethylcellulose, microcrystalline cellulose (e.g. Avicel® RC 591, methylcellulose); carraghenan, naturally occurring gums such as, acacia gum, arabic gum, xanthan gum, or gum tragacanth, and mixtures thereof e.g., gum acacia, celluloses such as, e.g., alginates and chitosans such as, e.g., sodium alginate, etc.

Examples of gel bases, viscosity-increasing agents or components which are able to take up exudate from a wound are: liquid paraffin, polyethylene, fatty oils, colloidal silica or aluminum, zinc soaps, glycerol, propylene glycol, tragacanth, carboxyvinyl polymers, magnesium-aluminum silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), and alginates including propylene glycol aginate.

Other examples of gels for use in a formulation according to the invention comprises hydrogels such as PEG (Poly Ethylene Glycol), dextransulphates, dextrose, heparansulphates, gelatins, or the like.

Examples of ointment bases are e.g. beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes.

Examples of hydrophilic ointment bases are solid macrogols (polyethylene glycols).

Other examples of ointment bases are triethanolamine soaps, sulphated fatty alcohol and polysorbates.

Examples of powder components are: alginate, collagen, lactose, powder which is able to form a gel when applied to a wound (absorbs liquid/wound exudate). Normally, powders intended for application on large open wounds must be sterile and the particles present must be micronized.

Examples of other excipients are polymers such as carmelose, sodium carmelose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetanyl glucoside, collagen, carrageenan, hyaluronates and alginates and kitosans.

Suitable dispersing or wetting agents are, for example, naturally occurring phosphatides, e.g., lecithin, or soybean lecithin; condensation products of ethylene oxide with e.g. a fatty acid, a long chain aliphatic alcohol, or a partial ester derived from fatty acids and a hexitol or a hexitol anhydride, for example polyoxyethylene stearate, polyoxyethylene sorbitol monooleate, polyoxyethylene sorbitan monooleate, etc.

The concentration of the EMD proteins and/or enamel matrix proteins in a pharmaceutical formulation according to the invention will, as the skilled person readily understands, vary depending on the intended use of the formulation. Typically, the concentration of the peptide in the pharmaceutical formulation is in the range of 0.01 to 100 mg/ml, such as 0.05 to 90 mg/ml, such as 0.5-80 mg/ml, such as 1 to 70 mg/ml, such as 5 to 65 mg/ml, such as 10 to 60 mg/ml, such as 15 to 55 mg/ml, such as 20 to 50 mg/ml, such as 25 to 45 mg/ml, such as 25 to 40 mg/ml, such as 26 to 39 mg/ml, such as 27 to 36 mg/ml, such as 27, 28, 29, 30, 31, 32, 33, 34, 35 or 36 mg/ml. The amount applied in vivo to a subject is typically about 10 ng/cm$^2$-0.1 mg/cm$^2$, such as about 1 µg/cm$^2$.

Purified Enamel Matrix Derivative (EMD) proteins contain 3 major protein fractions which are separable by High Pressure Liquid Chromatography (HPLC). These fractions are named fraction A, B and C, respectively. A typical weight ratio of the isolated and/or purified proteins is about 80/8/12 between the main protein peaks at 20, 14 and 5 kDa, respectively.

As mentioned above, the fraction C typically has a molecular weight of between approximately 3, 5 and 5 kDa, such as approximately 5 kDa, 4 kDa and 3.5 kDa, as determined by SDS PAGE electrophoresis. The fraction A typically has a molecular weight of approximately 20 kDa, as determined by SDS PAGE electrophoresis. The fraction B typically has a molecular weight of between approximately 6 kDa and 15 kDa, such as approximately 15 kDa, 12 kDa, 10 kDa and 6 kDa, as determined by SDS PAGE electrophoresis.

EMD proteins and/or enamel matrix proteins are composed of a number of proteins, such as amelogenins, enamelin, tuft protein, proteases, and albumin. Amelogenins, a major constituent of EMD proteins and/or enamel matrix proteins (up to approximately 90%), are a family of hydrophobic proteins derivable from a single gene by alternative splicing and controlled post secretory processing. They are highly conserved throughout vertebrate evolution and demonstrate a high overall level of sequence homology among all higher vertebrates examined (80%). In fact, the sequences of porcine and human amelogenin gene transcript differ only in 4% of the bases. Thus, enamel matrix proteins or EMD proteins, although of porcine origin, are considered "self" when encountered in the human body and can promote dental regeneration in humans without triggering allergic responses or other undesirable reactions.

In the present context, purified Enamel Matrix Derivative (EMD) proteins are thus defined as enamel matrix proteins comprising at least 60-70% amelogenins, such as at least 60, 61, 62, 63, 64, 65, 66, 67, 68, 69 or 70%, with a molecular weight of about 20-25 kDa, such as 20, 21, 22, 23, 24, or 25 kDa, or such as between 20-22, 20-24, or 20-23 kDa. In general, the weight ratio of the purified and/or isolated enamel matrix proteins is about 80/8/12, such as 75-85/5-12/5-15, or such as at least 80%, at least 8%, and at least 5%, between the main protein peaks of fraction A, B and C, respectively. Approximately 60-90%, such as at least 60, 61, 62, 63, 64, 65, 66, 67, 68, 69, 70, 80, 70-90, 60-70, 70-80, or 80-90% of the purified and/or isolated enamel matrix proteins are amelogenins and/or fragments or derivatives of amelogenin.

In the present invention, a local algorithm program is best suited to determine identity of the proteins. Local algorithm programs, (such as Smith-Waterman) compare a subsequence in one sequence with a subsequence in a second sequence, and find the combination of subsequences and the alignment of those subsequences, which yields the highest overall similarity score. Internal gaps, if allowed, are penalized. Local algorithms work well for comparing two multidomain proteins, which have a single domain or just a binding site in common.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al, Altschul, S. F. et al (1990)). Another preferred example is Clustal W (http://www.ebi.ac.uk/clustalw/). Each sequence analysis program has a default scoring matrix and default gap penalties. In general, a molecular biologist would be expected to use the default settings established by the software program used.

The amino acids in an EMD protein and/or enamel matrix protein may further be modified in terms of chemistry, isometry or in any other way as long as the sequences of the protein is intact. Modifications of the amino acids of the EMD protein and/or enamel matrix protein may increase the activity, stability, biocompatibility or clinical performance of the proteins, or reduce toxicity and adverse reactions to the proteins. Examples of chemical modifications include, but are not limited to, glycosylation and methylation. The amino acids may also be of all different types of stereoisomeric forms, such as D or L forms of amino acids, or S or R isomers. The amino acids in an EMD protein and/or enamel matrix protein of the invention may also be replaced by synthetic analogues thereof. The use of synthetic analogues may e.g. result in an EMD protein and/or enamel matrix protein that is more stable and less prone to degradation. Examples of unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-a-amino butyric acid*, L-g-amino butyric acid*, L-a-amino isobutyric acid*, L-e-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * is herein utilised to indicate the hydrophobic nature of the derivative whereas # is utilised to indicate the hydrophilic nature of the derivative, #* indicates amphipathic characteristics.

EMD proteins and/or enamel matrix proteins may further comprise N- and/or C-terminal tags comprising the amino acids His and/or Met. Met contains sulphur, which as previously explained facilitates binding to metal surfaces. His has a strong affinity for e.g. Ni and other metals. The use of these tags therefore has the advantage of enabling the proteins to attach to metal surfaces like titanium, zirconium, aluminium, tantalum, gold, surgical steel and nickel, or a metal oxide hydroxide and/or hydride surface etc. This is of great importance e.g. when EMD proteins and/or enamel matrix proteins are to be attached to a metal surface, such as when they are to be used to improve the biomineralization and/or osseointegration of a medical prosthetic device. The C- and/or N-terminal tags are also useful in the process of purification of produced proteins, as is well known to the skilled person. The use of an N-terminal and/or C-terminal tag also allows the proteins to be fully exposed, i.e. the tag is used for binding the protein to a surface and the rest of the protein is free for interactions with e.g. atoms, molecules, cells and tissue. The use of one tag in each end of EMD proteins and/or enamel matrix proteins may be useful during production of the proteins, allowing one end of the peptide being attached to a column during the purification of the protein of interest from incomplete protein products, while the other end of the protein may be used for binding to a surface of interest. Consequently, one preferred embodiment of the invention relates to formulation comprising an EMD proteins and/or enamel matrix proteins, further comprising an N-terminal and/or a C-terminal histidine tag. Such a tag may as previously mentioned, comprise methionine and/or histidine residues, which have been attached to an EMD proteins and/or enamel matrix proteins according to the invention. In a preferred embodiment, this tag comprises 3 or more residues, such as between 3-5 or 5-10 residues. A tag can comprise any amount of residues, which still provides for a stable formulation together with the EMD protein and/or enamel matrix protein according to the invention not affecting the secondary structure of the EMD protein and/or enamel matrix protein in a negative manner. Preferably this histidine tag consists of five histidine residues. In another preferred embodiment the EMD protein and/or enamel matrix protein comprises an N-terminal and/or C-terminal methionine tag, preferably consisting of five methionine residues. In another preferred embodiment, the formulation comprises EMD proteins and/or enamel matrix proteins comprising a methionine tag in its C- or N-terminal end and a histidine tag in the other end.

In one embodiment, the EMD proteins and/or enamel matrix proteins are produced instead of isolated from a natural source, e.g. by synthetic production or biosynthesis. The EMD proteins and/or enamel matrix proteins, or fragments thereof may be produced by any known method for production of peptides, such as synthetic production by chemical synthesis. Synthetic production also allows the use of amino acid analogues which may improve the stability of the proteins or fragments produced. The skilled person knows the methods that are available for the synthesis of an amino acid sequence.

Preferably, bioproduction may be used as a method for producing the EMD proteins and/or enamel matrix proteins, or fragments thereof. Bioproduction means the production of an amino acid sequence in a biological system, such as a cell culture or in microbial cells, e.g. bacterial cells. For bioproduction, it is necessary to construct the corresponding nucleic acid sequence encoding a specific amino acid sequence. The skilled person readily knows how to construct such a nucleic acid sequence once a specific amino acid sequence to be synthesized is determined upon, and how to produce an EMD protein and/or enamel matrix protein, or fragments thereof and purify it from the system used to produce it (see e.g. Svensson J, Andersson C, Reseland J E, Lyngstadaas S P, Bulow L. Histidine tag fusion increase expression levels of active recombinant Amelogenin in *Escherichia coli*. (Protein Expr Purif, 48; 134-41 (2006)).

A medical prosthetic device in the present context relates to any device intended to be implanted into the body of a vertebrate animal, in particular a mammal, in particular a human. Medical prosthetic devices in the present context may be used to replace anatomy and/or restore any function of the body. Non-limiting examples of such devices are medical devices that replaces anatomy or restores a function of the body such as the femoral hip joint; the femoral head; acetabular cup; elbow including stems, wedges, articular inserts; knee, including the femoral and tibial components, stem, wedges, articular inserts or patellar components; shoulders including stem and head; wrist; ankles; hand; fingers; toes; vertebrae; spinal discs; artificial joints; dental implants; ossiculoplastic implants; middle ear implants including incus, malleus, stapes, incus-stapes, malleus-incus, malleus-incus-stapes; cochlear implants; orthopaedic fixation devices such as nails, screws, staples and plates; heart valves; pacemakers; catheters; vessels; space filling implants; implants for retention of hearing aids; implants for external fixation; and also intrauterine devices (IUDs); and bioelectronic devices such as intracochlear or intracranial electronic devices.

The formulations of the present invention may also comprise particles, example of particles are porous particles having a pore size in the range of 100 to 500 microns in diameter.

Administration

A pharmaceutical, dental and/or cosmetic formulation according to the present invention can be used in promoting and/or inducing regeneration of hard tissue, tissue mineralization, bone growth and/or bone regrowth, regeneration of dentin, cementogenesis, and/or binding between parts of living mineralized tissue, for bonding of a piece of living mineralized tissue to a bonding site on a piece of other living tissue, for endorsing binding between hard tissues, and/or for filling a mineralized wound cavity and/or tissue defect following from a procedure and/or trauma.

A pharmaceutical, dental and/or cosmetic formulation according to the present invention can alternatively and/or additionally be used in promoting and/or inducing regeneration of soft tissue and/or for treating and/or preventing an inflammation and/or infection and/or for treating SIRS.

Consequently, the present invention further relates to the use of a pharmaceutical, dental and/or cosmetic formulation comprising enamel matrix proteins and/or enamel matrix derivative (EMD) proteins, wherein said formulation comprises no more than 6 weight % (wt) sterilized propylene glycol alginate (PGA) and wherein said sterilized PGA, has a weight average molecular weight ($M_W$) above 130 kDa, such as above or equal 135, 140, 150, 180 or 185 kDa, for the manufacture of a pharmaceutical composition for promoting and/or inducing regeneration of hard tissue, tissue mineralization, bone growth and/or bone regrowth, regeneration of dentin, cementogenesis, and/or binding between parts of living mineralized tissue, for bonding of a piece of living mineralized tissue to a bonding site on a piece of other living tissue, for endorsing binding between hard tissues, and/or for filling a mineralized wound cavity and/or tissue defect following from a procedure and/or trauma, as well as for promoting and/or inducing regeneration of soft tissue and/or for treating and/or preventing an inflammation and/or infection and/or for treating SIRS.

Also, a method is envisioned for promoting and/or inducing regeneration of hard tissue, tissue mineralization, bone growth and/or bone regrowth, regeneration of dentin, cementogenesis, and/or binding between parts of living mineralized tissue, for bonding of a piece of living mineralized tissue to a bonding site on a piece of other living tissue, for endorsing binding between hard tissues, and/or for filling a mineralized wound cavity and/or tissue defect following from a procedure and/or trauma, as well as promoting and/or inducing regeneration of soft tissue and/or for treating and/or preventing an inflammation and/or infection and/or for treating SIRS, comprising administering a pharmaceutical, dental and/or cosmetic formulation comprising enamel matrix proteins and/or enamel matrix derivative (EMD) proteins, wherein said formulation comprises no more than 6 weight/volume % (w/v %) sterilized propylene glycol alginate (PGA) and wherein said sterilized PGA has a weight average molecular weight ($M_W$) above 130 kDa, such as above or equal 135, 140, 150, 180 or 185 kDa, to a patient in need thereof.

A pharmaceutical, dental and/or cosmetic formulation, comprising enamel matrix proteins and/or enamel matrix derivatives (EMD) proteins and sterilized propylene glycol alginate (PGA), wherein the weight average molecular weight ($M_W$) of the sterilized PGA is above 130 kDa, such as above or equal 135, 140, 150, 180 or 185 kDa, may be administered to a subject in need thereof by any suitable route depending on the tissue which the peptide is to be administered to, for example by topical (dermal), oral, buccal, nasal, aural, rectal or vaginal administration, or by administration to a body cavity such as, e.g., a tooth root, a tooth root canal or a bone fracture. Furthermore, a formulation of the invention may be adapted to administration in connection with surgery, e.g. in connection with incision within the body. The formulations of the invention may also be administered via local injections, by application in a gel or via a medical device, such as a medical prosthetic device, e.g. a graft, scaffold or bioglass material. It is also possible to administer the formulations of the invention via alginate or citosan (slow release) beads, a toothpaste, in a shampoo, in a dental filling material. If administrated locally a pharmaceutical formulation of the invention comprising EMD proteins and/or enamel matrix proteins and PGA having a high average molecular weight, as defined above, into e.g. a fracture, periodontal defect, extraction alveolas, or sinus lift procedure, the proteins may improve and/or speed up bone healing.

The formulations may be encapsulated and delivered orally by ingestion, by the nasal cavity or lungs by inhalation or by injection into the blood, into the spinal fluid, into joints or intraperitoneally as a slow release depot.

In another aspect, the invention relates to the use of a pharmaceutical, dental and/or cosmetic formulation, comprising enamel matrix proteins and/or enamel matrix derivatives proteins (EMD) and sterilized propylene glycol alginate (PGA), wherein the weight average molecular weight ($M_W$) of the sterilized PGA is above 130 kDa, such as above or equal 135, 140, 150, 180 or 185 kDa, for the preparation of a medicament for the induction of biomineralization. In particular, the invention also relates to the use of a pharmaceutical formulation comprising EMD proteins and/or enamel matrix proteins and PGA having a high weight average molecular weight, as defined above, for the preparation of a medicament for the formation and/or regeneration of bone. In a particular embodiment, the invention also relates to the use of a pharmaceutical formulation comprising EMD proteins and/or enamel matrix proteins and PGA having a high weight average molecular weight, as defined above, for the preparation of a medicament for the formation and/or regeneration of bone cartilage, cementum and/or dental tissue. The pharmaceutical formulations of the invention comprising EMD proteins and/or enamel matrix proteins and PGA having a high weight average molecular weight, as defined above, may also be used for the preparation of medicaments for the treatment of osteoporosis, fractures, periodontitis, traumas, bone metabolic syndrome, pulitis, dental apical lesions, etc.

The pharmaceutical, dental and/or cosmetic formulation, comprising enamel matrix proteins and/or enamel matrix derivatives (EMD) proteins and sterilized propylene glycol alginate (PGA), wherein the weight average molecular weight ($M_W$) of the sterilized PGA is above 130 kDa, such as above or equal 135, 140, 150, 180 or 185 kDa, may also be used for the preparation of a medicament for the healing of bone fractures.

One aspect the invention also relates to pharmaceutical, dental and/or cosmetic formulation, comprising enamel matrix proteins and/or enamel matrix derivatives proteins (EMD) and sterilized propylene glycol alginate (PGA), wherein the weight average molecular weight ($M_W$) of the sterilized PGA is above 130 kDa, such as above or equal 135, 140, 150, 180 or 185 kDa, for use for the induction of biomineralization. For example a pharmaceutical formulation of the invention comprising EMD proteins and/or enamel matrix proteins and PGA having a high average molecular weight, as defined above, may be used for the preparation of a medicament for the formation and/or regeneration of bone cartilage, cementum and/or dental tissue.

In another aspect, the invention relates to a pharmaceutical formulation of the invention comprising EMD proteins and/or enamel matrix proteins and PGA having a high weight average molecular weight, as defined above, for use for the formation and/or regeneration of bone.

In yet another aspect, the invention relates to a pharmaceutical formulation of the invention comprising EMD proteins and/or enamel matrix proteins and PGA having a high weight average molecular weight, as defined above, for use for the healing of bone fractures.

The EMD proteins and/or enamel matrix proteins may also be used in combination with natural proteins inducing mineral precipitation and/or biomineralization and/or bone formation, such as BMPs. It is also possible to use a combination of two or more proteins for the induction and/or stimulation of mineral precipitation, including biomineralization.

A pharmaceutical formulation of the invention comprising EMD proteins and/or enamel matrix proteins and PGA having a high weight average molecular weight, as defined above, may also be used for the fusion of two biomineralized structures, or the fusion of a biomineralized structure with another material. Examples of such materials include implantable biomaterials, such as titanium and steel, bioglass, calcium phosphates, apatite etc. Other examples include column material, filter materials etc.

A supplemented formulation according to the invention is a formulation, which can further comprise cellulose derivatives and alginates, such as carboxymethyl celluloses and PGA.

The present invention also relates to a formulation consisting enamel matrix proteins and/or enamel matrix derivative (EMD) proteins, wherein at least 60-70%, such as 60, 61, 62, 63, 64, 65, 66, 67, 68, 69 or 70%, of the proteins have a molecular weight between 16-40 kDa, such as above 20 kDa, such as 16, 17, 18 or 19 kDa, and no more than 3 to 6 weight/volume % (w/v %), such as 3, 4, 5, or 6 w/v %, of a sterilized propylene glycol alginate (PGA) with a weight average molecular weight of above 130 kDa, such as above or equal 135, 140, 150, 180 or 185 kDa. The present invention also relates to a formulation essentially consisting enamel matrix proteins and/or enamel matrix derivative (EMD) proteins, wherein at least 60-70%, such as 60, 61, 62, 63, 64, 65, 66, 67, 68, 69 or 70%, of the proteins have a molecular weight between 16-40 kDa, such as above 20 kDa, such as 16, 17, 18, 19 or 20 kDa, and no more than 3 to 6 weight/volume % (w/v %), such 3, 4, 5, or 6 w/v %, of a sterilized propylene glycol alginate (PGA) with a weight average molecular weight of above 130 kDa, such as above or equal 135, 140, 150, 180 or 185 kDa.

EXPERIMENTAL SECTION

Example 1

The Weight Average Molecular Weight ($M_W$)

The weight average molecular weight was been determined according to the analysis method AM-S01 using a GPC (Agilent) and the following parameters:
Eluent: Phosphate Buffer pH 7.0
Precolumn Columns: PSS Suprema 10 µm 100 Å 8×50 mm
PSS Suprema 10 µm 100 Å 8×300 mm
PSS Suprema 10 µm 1000 Å 8×300 mm
PSS Suprema 10 µm 100 Å 8×300 mm
Pump: Agilent 1100
Flow 1.0 ml/min
Autosampler: Agilent 1100 with 5 oµl inject volume
Sample conc. 2.0, 3.0 g/L
Temp: 23° C.
Detector Aglient 1100 RI
Calculation: PSS WinGPC Unity Ver. 7.20
Calibration based on conventional calibration with Pollulan molar mass standards The weight average molecular weight of non-sterilized PGA since 2002 to 2009 and Kelcoloid® O is disclosed in table 1.

TABLE 1

| PGA | $M_n$ [kDa] | $M_w$ [kDa] | $M_z$ [kDa] | Used in Production period |
|---|---|---|---|---|
| PGA 107 | 64.7 | 211 | 574 | 2002-2004 |
| PGA 109 | 66.5 | 212 | 658 | 2004-2005 |
| PGA 110 | 68.0 | 219 | 630 | 2005-2007 |
| C5966 | 71.4 | 244 | 707 | 2008-2009 |
| Kelcoloid® 9B02535 | 68.6 | 416 | 1840 | 2010 |

This table shows that the prior PGAs used had a weight average molecular weight between 210-245 kDa, meaning about 230 kDa or no more than 245 kDa. Furthermore, this table shows that the difference between $M_W$ and $M_Z$ is much higher for Kelcoloid® O 9B02535 than the previously used PGAs.

Example 2

Sterilized PGA, which is used in Emdogain formulation, is obtained from e-beam sterilization of non-sterilized PGA according to the ISO 1137-2 (2006) recommendation. The sterilization method comprises the following steps:
1. The sterility assurance level (SAL) $10^{-6}$ (one milliomod) is applied for one sterilization unit of PGA (100 g PGA/pouch)
2. The total bioburden is calculated for this sterilization unit (100 g PGA/pouch): total bioburden=100 g*CFU/g-->if this sterilization unit change for example packing only 50 g PGA the total bioburden decreases
3. Accordingly, this total bioburden VDmax 25 is applied-->min 25 kGy PGA does not undergo crosslinking in the course of e-beam irradiation. The dominant process caused by the e-beam irradiation is a chain rupture. Hence, in this case the change in weight average molecular weight ($M_W$) with variation of e-beam dose (R) can be simplified by charlesby equation (Equation 1). The initial weight average molecular weight ($M_{W0}$) of PGA, the applied e-beam dose (R) and radiolitic yield ($G_s$) determine basically the molecular weight of sterilized PGA ($M_W$) (see e.g. FIG. 8).

$$\frac{1}{M_W} = \frac{1}{M_{W0}} + \frac{G_S R}{1.92 \times 10^6} \qquad \text{Equation 1}$$

The $G_s$ is constant for chemically identical PGA. Calculated values for Manucol ($G_E M$) ester B and Kelcoloid® O ($G_{sK}$) PGA were almost identical within the deviation: $G_{sM}$=2.37±0.15; $G_{sK}$=2.25±0.07[kDa*kGy]$^{-1}$ Since e-beam dose detection error range is 2 kGy, the delivered sterilization e-beam dose can be found is in the narrow range of R=26.4-28.4 kGy (providing a good security margin), the initial $M_{W0}$ determines mainly the $M_W$ of sterilized PGA. $M_{W0}$=$M_W$ of non-sterilized PGA. This is the reason why the initial molecular weight should be high. This is the driving force to have good thickening properties.

(T. Q Nguyen, H. H Kausch, J. App. Polym. Sci. 29 (1984), p. 455)

(A. Schiltz, et al, Revue Phys. Appl. 19 (1984)439 (439-444))

Example 3

The degradation of PGA was studied by C. J. Gray. A. J. Griffiths, D. L. Stevenson, J. F. Kennedy; *Studies on the Chemical Stability of Propylene Glycol alginates Ester, Carbohydrate Polymers*, 1990, 12, 419-430.

They identified two types of degradation:
1) The hydrolysis of ester bonds providing carboxylic acid and propylene glycol (pH change)
2) The degradation of the glycosidic linkages in the polysaccharide backbone accompanied by decrease in viscosity They found that under acidic conditions, the ester group in PGA are stable to hydrolysis and only hydrolytic degradation of polysaccharide backbone occurs. This statement, however, was not proved under moderate acidic conditions (~pH 3-5). The polymer backbone hydrolytic rupture occurs simultaneously with the hydrolysis of ester and both the pH and the viscosity decreases.

The overall hydrolysis rate of ester can be written as a sum of the individual rate of acid catalyzed rate: $k_A$[ester][H$^+$], neutral rate: $k'_{H_2O}$[ester] and base catalyzed hydrolysis rate: $k_B$[ester][OH$^-$]:

$$\text{Rate(overall)} = -\frac{d[\text{ester}]}{dt} = k_A[\text{ester}][\text{H}^+] + k'_{H_2O}[\text{ester}] + k_B[\text{OH}^-] \quad \text{Equation 1}$$

wherein $k_A$; $k'_{H_2O}$; $k_B$ are the reaction rate constants, [ester]; [H$^+$]; [OH$^-$] are the ester, proton (hydrogen ion) and hydroxyl ion concentration respectively.

Under acidic conditions, the neutral and base catalyzed hydrolysis is can be ignored compared to the acid catalyzed reaction and Equation 1 is can therefore be simplified to $$-\frac{d[\text{ester}]}{dt} = k_A[\text{ester}][\text{H}^+] \quad \text{Equation 2}$$

There is parity between the production of carboxylic acid and consumption of the ester (FIG. 3).

Consequently, the rate of the consumption of the ester is equal to the production of the carboxylic acid and Equation 2 can be converted into $$\frac{d[\text{acid}]}{dt} = k_A[\text{ester}][\text{H}^+] \quad \text{Equation 3}$$

The overall rate of the acid production is considered to be proportional to d[H$^+$]/dt giving $$\frac{d[\text{H}^+]}{dt} = k_A[\text{ester}][\text{H}^+] \quad \text{Equation 4}$$

PGA hydrolysis in Emdogain is analogue to ester hydrolyses. The concentration of [H$^+$] between pH 5 and pH 3 varies two orders of magnitudes. The change of the ester concentration in the period from the initial pH (~pH 5) to when the pH is decreased to 3.0 is much smaller extend than the increase of [H$^+$], subsequently, the variation of [H$^+$] represent a bigger impact on the overall rate than the change of the ester concentration. For simplicity, [ester] is involved in the reaction rate constant $k_A$ providing k' pseudo first rate constant.

$$\frac{d[\text{H}^+]}{dt} = k'[\text{H}^+] \quad \text{Equation 5}$$

Considering that the initial [H$^+$] is [H$_0^+$], the integration of Equation 5 gives $$\int_{H_0^+}^{H^+} \frac{d[\text{H}^+]}{[\text{H}^+]} = \int_{t=o}^{t} k' dt \quad \text{Equation 6}$$

⇓

$$\ln[\text{H}^+] = k't + \ln[\text{H}_0^+] \quad \text{Equation 7}$$

Being pH=−log [H$^+$] and ln [H$^+$]=−2.3025*pH, Equation 7 can be written as $$\text{pH} = -k''t + \text{pH}_0 \quad \text{Equation 8}$$

Where k"=2.3025*k' is the pseudo first order reaction rate constant of sterilized PGA hydrolysis in Emdogain, t is storage time of Emdogain, pH is the actual pH in time=t and pH$_0$ is the initial pH.

The Equation 8 shows that there is linear correlation between the pH and storage time (t) and where the slop is the pseudo first order reaction rate constant (k"). Indeed, as long as the pH reaches the low controlled limit of specification (pH 3.5), this linearity can be presumed (FIG. 4).

Beyond pH 3.5 the equilibrium behavior of acid catalyzed desesterification and esterification should be taken into account. Approaching the equilibrium pH (around pH 2.7-2.8) the pH vs. time curve flattens (FIG. 5). Since the specified acceptance limit of product is pH 3.5, Equation 8 can be used to describe the overall rate of pH change within the specified pH values.

Effect of the Sterilized PGA Concentration on the Reaction Rate Constant

In order to simplify the model to pseudo first order reaction kinetic equation (from Equation 4 to Equation 5), the concentration of ester [ester] was merged with the reaction rate constant $k_A$. In the stability protocols of Emdogain (Biora STP documents), the ester concentration was not followed. Following the same consideration when Equation 4 was converted to Equation 5, the change of ester concentration could not be extended of order of magnitude and it can be replaced by the sterilized PGA concentration [sterilizedPGA].

$$k''=2.3025*k_A[\text{ester}] \approx k''=k'_A[\text{sterilizedPGA}] + \text{Const.} \quad \text{Equation 9}$$

wherein $k'_A$=2.3025*$k_A$ acidic PGA hydrolysis rate constant and Const. is the zero sterilized PGA concentration esterification rate constant. This latter refers to the acid catalyzed esterification when only the corresponding carboxylic acid and alcohol are present in the solution.

The linear regression between k" and [sterilizedPGA] gives $$k'' = 0.0205 * [sterilizedPGA] - 0.0914 \quad \text{Equation 10}$$

From Equation 9 and 14 a rough estimation the time when the pH decrease to 3.5 from the initial $pH_0$ can be done (pH determined shelf life or durability of Emdogain $t_{pH3.5}$).

$$t_{pH3.5} = \frac{pH_0 - 3.5}{0.0205 * [sterilizedPGA] - 0.0914} \quad \text{Equation 11}$$

The applied sterilized PGA concentration [sterilizedPGA] for 24 months durability calculated from Equation 14 is proved the critical concentration keeping the pH within the spec requirement over 24 months without exposing the product to higher temperature. The higher temperature accelerate the hydrolysis process The Effect of Temperature on the Reaction Rate Constant The effect of the temperature on the pH drop is evident. Exposure of Straumann® Emdogain to elevated temperature significantly accelerates the overall rate of pH drop. The reaction rate constant (k") varies with temperature (T) according to Arrhenius equation $$k'' = Ae^{\frac{-E_a}{RT}} \quad \text{Equation 12}$$

Written in logarithmic form $$\log k'' = \log A - \frac{E_a}{RT} \quad \text{Equation 13}$$

wherein R=8.314472 J/(K*mol)—universal gas constant; A is frequency factor; $E_a$ is the activation energy of the reaction [J/mol]; T is the temperature in Kelvin.

According to Equation 10 there is linear relationship between $$\log k'' \Rightarrow \frac{1}{T} \quad \text{Equation 14}$$

which permits to determine the log A and $E_a$/R constants from linear regression lines. The temperature dependency is summarized in Table 2.

TABLE 2

| pseudo first order reaction rate constant vs. storage temperature | | | | | |
|---|---|---|---|---|---|
| temp [° C.] | 37 | 30 | 20.00 | 5.00 | −18.00 |
| k" | 0.9252 | 0.5607 | 0.1641 | 0.031367 | 0.00200 |
| log k" | −0.03376 | −0.25127 | −0.78489 | −1.50353 | −2.69897 |
| 1/T [1/K] | 0.003224 | 0.003299 | 0.003411 | 0.003595 | 0.003919 |

Including the temperature and the PGA concentration dependency and the exposed temperature accelerated acidification, 6 weight/volume % (w/v %) PGA is determined as threshold for pH stability of the EMD-PGA system. For the applicability and clinical test proved the viscosity of the formulation needs 3.0-4.0 Pa*s (22° C., 19 1/s). For this purpose the threshold of the weight average molecular weight of PGA should be above 130 kDa measured by GPC to Pollulan calibration standard.

Example 4

Storage Stability of EMD Formulations

Sample Preparation:
EMD Solution

EMD solution having a concentration of 33 mg/ml was prepared in normal production line according to normal EMD bulk solution production. The solution was withdrawn from the production line after the sterile filtration. The EMD solution comprises acetic acid and water and the pH of the solution is between 4.9 to 5.

PGA

Kelcoloid® O was purchased from FMC Biopolymer. The $M_w$ was determined as already described above. The obtained $M_W$ value is indicated in Table 1 above The PGA was sterilized by e-beam sterilization. The equipment used: sterigenics San Diego, delivered e-beam dose: 25-30 kGy. The obtained sterilized PGA has a $M_W$=184 kDa+−12 kDa Emdogain Sample Preparation:

The obtained sterilized PGA (30.0 g) was added slowly to the EMD bulk solution (500 mL) under laminal air flow (LAF) at ambient temperature (around 20° C. The solution was stirred and the stirring was continued for over 24 h and then stopped. The Emdogain formulation samples were transferred into sterile sample tubes (50 mL) under LAF. One sample was withdrawn and the pH and the viscosity were measured:

viscosity=3.0 Pa·s (22° C., 18.9 1/s) (Anton Paar MRC Physica 300 rheometer, configuration: CP-25-2-->Serial N° 12513)

pH 4.70 (Metrohm 780 pH meter equipped with Entrich pH probe N° 6.00226.100)

The obtained samples were immediately placed into a fridge after preparation. The temperature of the fridge was adjusted to +4° C. The temperature was controlled in the approximate of the sample. The deviation of the temperature has never exceeded the +−2.0° C.

The pH of samples was measured over fourteen month (see FIG. 9)

Reference Samples:

pH stability data is withdrawn from Emdogain stability program. Data was chosen from a Emdogain sample which was prepared using e-beam sterilized PGA $M_W$=117 kDa. the name of the reference sample is E7254

Initial values: Viscosity: 3.0 Pa·s (22° C., 18.9 1/s) and pH 4.5

Raw PGA: $M_W$ 219 kDa
sterile (e-beam treated) PGA: $M_W$ 117 kDa

The pH of the reference sample was measured over 24 months (see FIG. 9)

REFERENCES

1. Gestrelius S, Lyngstadaas S P, Hammarström L. Emdogain—periodontal regeneration based on biomimicry. Clin Oral Invest 4:120-125 (2000)
2. Hammarström et al., 1997, Journal of Clinical Periodontology 24, 658-668
3. Lyngstadaas et al., 2001, Journal of Clinical Periodontology 28, 181-188
4. U.S. Pat. No. 467,032
5. EP-B-0 337 967

6. EP-B-0 263086
7. EP-B-1059934
8. EP-B-1153610
9. WO 01/97834
10. WO 00/53197
11. WO 00/53196
12. WO 03/024479
13. WO 02/080994
14. U.S. Pat. No. 5,098,891
15. D. J. McHugh—HYPERLINK http://www.fao.org/docrep/x5822e/x5822e04.htm
16. Svensson J, Andersson C, Reseland J E, Lyngstadaas S P, Bulow L. Histidine tag fusion increase expression levels of active recombinant Amelogenin in *Escherichia coli*. Protein Expr Purif, 48; 134-41 (2006)
17. C. J. Gray. A. J. Griffiths, D. L. Stevenson, J. F, Kennedy; Studies on the Chemical Stability of Propylene Glycol alginates Ester, Carbohydrate Polymers, 1990, 12, 419-430
18. T. Q Nguyen, H. H Kausch, J. App. Polym. Sci. 29 (1984), p. 455-464
A. Schiltz, et al, Revue Phys. Appl. 19 (1984) 439 (439-444)
19. Hammarström et al., "Periodontal regereration in a buccal dehiscene model in monkeys after application of enamel matrix proteins", J Clin Periodontol 1997 (24) 669-677
20. Lyngstadaas et al., "Enamel matrix proteins; old molecules for new applications", Orthod Craniofac Res 2009 Aug. 12(3) 243-253
21. US 20060147395 A1
22. EP-A2-1120428
23. Gestrelius et al., "Formulation of enamel matrix derivative for surface coatings", J Clin Periodontol 1997 (24) 678-684
24. Heijl et al., J Clin Periodonol 1997 (24) 693-696

The invention claimed is:

1. A pharmaceutical, dental and/or cosmetic formulation comprising enamel matrix proteins and/or enamel matrix derivative (EMD) proteins and a sterilized propylene glycol alginate, wherein said formulation comprises no more than 6 weight/volume % (w/v %) sterilized propylene glycol alginate (PGA), wherein the weight average molecular weight (Mw) of the PGA prior to sterilization is at least 250 kDa, and wherein said sterilized PGA has a weight average molecular weight (Mw) above 130 kDa.

2. A pharmaceutical, dental and/or cosmetic formulation according to claim 1, wherein the weight average molecular weight (Mw) of the sterilized PGA is in the range of between 130-250 kDa.

3. A pharmaceutical, dental and/or cosmetic formulation according to claim 1, comprising sterilized PGA in the range of 3 weight/volume % (w/v %) to 6 w/v % with a weight average molecular weight above 130 kDa.

4. A pharmaceutical, dental and/or cosmetic formulation according to claim 1, wherein the weight average molecular weight (Mw) of the sterilized PGA is above or equal to 185 kDa.

5. A pharmaceutical, dental and/or cosmetic formulation according to claim 1, wherein the sterilized PGA is obtained from e-beam sterilization of non-sterilized PGA with an initial weight average molecular weight (Mwo) of at least 250 kDa.

6. A pharmaceutical, dental and/or cosmetic formulation according to claim 5, wherein the sterilized PGA is obtained from e-beam sterilization of non-sterilized PGA with an initial weight average molecular weight (Mwo) in the range of 250 to 500 kDa.

7. A pharmaceutical, dental and/or cosmetic formulation according to claim 5, wherein the applied e-beam sterilization dose is selected from a dose in the range of 25 to 30 kGy.

8. A pharmaceutical, dental and/or cosmetic formulation according to any claim 1, wherein the enamel matrix proteins and/or enamel matrix derivative (EMD) proteins comprise at least 60-70% amelogenin, having an average molecular weight selected from the group consisting of between 18 and 25 kDa.

9. A pharmaceutical, dental and/or cosmetic formulation according to claim 1, wherein said formulation has a pH above 3.5 over a period of at least 18 months.

10. A pharmaceutical, dental and/or cosmetic formulation according to claim 1, wherein said formulation has a pH above 3.5 at a temperature range of 2 to 8° C.

11. A pharmaceutical, dental and/or cosmetic formulation according to claim 1, wherein the formulation further comprises one or more pharmaceutically acceptable excipient(s), pharmaceutically acceptable carrier(s), or a combination thereof.

12. A pharmaceutical, dental and/or cosmetic formulation according to claim 1, wherein the amount of the enamel matrix proteins and/or enamel matrix derivative (EMD) proteins is in the range of 93% to about 98%, by weight/volume, based on the total combined weight of the matrix proteins and/or enamel matrix derivative (EMD) proteins and the sterilized PGA, not including other excipients.

13. A pharmaceutical, dental and/or cosmetic formulation according to claim 1, additionally comprising one or more non-enamel matrix proteins and/or enamel matrix derivative (EMD) proteins active agents.

14. A pharmaceutical, dental and/or cosmetic formulation according to claim 1, comprising at least two surface stabilizers.

15. A pharmaceutical, dental and/or cosmetic formulation according to claim 14, wherein the surface stabilizer is selected from the group consisting of anionic surface stabilizer, cationic surface stabilizer, zwitterionic surface stabilizer and ionic surface stabilizer.

16. A pharmaceutical, dental and/or cosmetic formulation according to claim 1, for use in medicine.

17. A pharmaceutical, dental and/or cosmetic formulation according to claim 1, wherein the formulation is formulated for administration selected from the group consisting of oral, pulmonary, rectal, opthalmic, colonic, parenteral, intracisternal, intravaginal, intraperitoneal, local, buccal, nasal, and topical administration.

18. A pharmaceutical, dental and/or cosmetic formulation according to claim 1, formulated into a dosage form selected from the group consisting of liquid dispersions, oral suspensions, gels, aerosols, ointments, creams, controlled release formulations, fast melt formulations, lyophilized formulations, tablets, capsules, delayed release formulations, extended release formulations, pulsatile release formulations, and mixed immediate release and controlled release formulations.

19. A pharmaceutical, dental and/or cosmetic formulation according to claim 1 for use in promoting and/or inducing regeneration of hard tissue, tissue mineralization, bone growth and/or bone regrowth, regeneration of dentin, cementogenesis, and/or binding between parts of living mineralized tissue, for bonding of a piece of living mineralized tissue to a bonding site on a piece of other living tissue, for endorsing binding between hard tissues, and/or for filling a mineralized wound cavity and/or tissue defect following from a procedure and/or trauma.

20. A pharmaceutical, dental and/or cosmetic formulation according to claim 1 for use in promoting and/or inducing regeneration of soft tissue and/or for treating and/or preventing an inflammation and/or infection and/or for treating SIRS, for promoting and/or inducing regeneration of hard tissue, tissue mineralization, bone growth and/or bone regrowth, regeneration of dentin, cementogenesis, and/or binding between parts of living mineralized tissue, for bonding of a piece of living mineralized tissue to a bonding site on a piece of other living tissue, for endorsing binding between hard tissues, and/or for filling a mineralized wound cavity and/or tissue defect following from a procedure and/or trauma.

21. A method comprising administering to a patient a therapeutic amount of the formulation of claim 1.

22. The method according to claim 21, further comprising the following steps:
   a. isolating enamel matrix proteins and/or enamel matrix derivative (EMD) proteins from a developing mammal's teeth,
   b. e-beam sterilizing non-sterilized PGA with an initial weight average molecular weight (Mwo) above 250 kDa with a dose in the range of 25 to 30 kGy, and
   c. mixing the product obtained from a. and the product obtained from b.

23. A pharmaceutical, dental and/or cosmetic formulation, comprising enamel matrix proteins and/or enamel matrix derivative (EMD) proteins and sterilized propylene glycol alginate (PGA) with a weight average molecular weight above 130 kDa, wherein said formulation is produced by a process comprising the following steps:
   a. isolating enamel matrix proteins and/or enamel matrix derivative (EMD) proteins from a developing mammal's teeth,
   b. e-beam sterilizing non-sterilized PGA with an initial weight average molecular weight (Mwo) in the range of 250 to 500 kDa with a dose in the range of 25 to 30 kGy, and
   c. mixing the product obtained from a. and the product obtained from b.

* * * * *